United States Patent
Aubé

(10) Patent No.: US 7,533,854 B2
(45) Date of Patent: May 19, 2009

(54) BAG SUPPORT

(76) Inventor: François Aubé, 218, Solange, Brigham, Quebec (CA) J2K 4R1

( * ) Notice: Subject to any disclaimer, the term of this patent is extended or adjusted under 35 U.S.C. 154(b) by 0 days.

(21) Appl. No.: 11/453,965

(22) Filed: Jun. 16, 2006

(65) Prior Publication Data
US 2006/0284036 A1 Dec. 21, 2006

(30) Foreign Application Priority Data
Jun. 16, 2005 (GB) ................................ 0512243.7

(51) Int. Cl.
*B65B 67/12* (2006.01)
(52) U.S. Cl. .................... 248/95; 248/218.4; 248/230.7
(58) Field of Classification Search .................. 248/95, 248/218.4, 219.4, 230.1, 311.3, 229.16, 229.26, 248/228.7, 231.81, 230.7, 68.1; 211/107, 211/196, 205, 208
See application file for complete search history.

(56) References Cited
U.S. PATENT DOCUMENTS

| | | | | |
|---|---|---|---|---|
| 582,086 A | * | 5/1897 | Poole et al. ................... 211/22 |
| 3,332,654 A | * | 7/1967 | Jacobson ................... 211/107 |
| 3,900,110 A | * | 8/1975 | Soroka ...................... 211/113 |
| 5,320,312 A | * | 6/1994 | Hoenninger ............... 248/68.1 |
| 5,356,107 A | * | 10/1994 | Sinohuiz .................. 248/311.2 |
| 6,409,131 B1 | * | 6/2002 | Bentley et al. ........... 248/219.4 |
| 6,648,290 B1 | * | 11/2003 | Aleman .................. 248/311.2 |

\* cited by examiner

*Primary Examiner*—Ramon O Ramirez

(57) ABSTRACT

A bag support for supporting a bag, the bag support being mountable to a post, the bag having a pouch and a hook extending from the pouch. The bag support includes: a support body; a mounting clip for mounting the bag support to the post, the mounting clip including a pair of clip jaws extending substantially outwardly from the support body in a spaced apart relationship relatively to each other, the clip jaws defining a clip plane extending therebetween, the clip plane being substantially parallel to both of the clip jaws, the clip plane defining a longitudinal direction extending substantially perpendicularly to the clip plane; and a hook receiving element extending from the support body, the hook receiving element defining a hook receiving aperture, the hook receiving aperture being substantially parallel to the clip plane. Inserting said post substantially longitudinally between said clip jaws allows the insertion of the hook into said hook receiving aperture so that the hook is substantially parallel to the post.

11 Claims, 3 Drawing Sheets

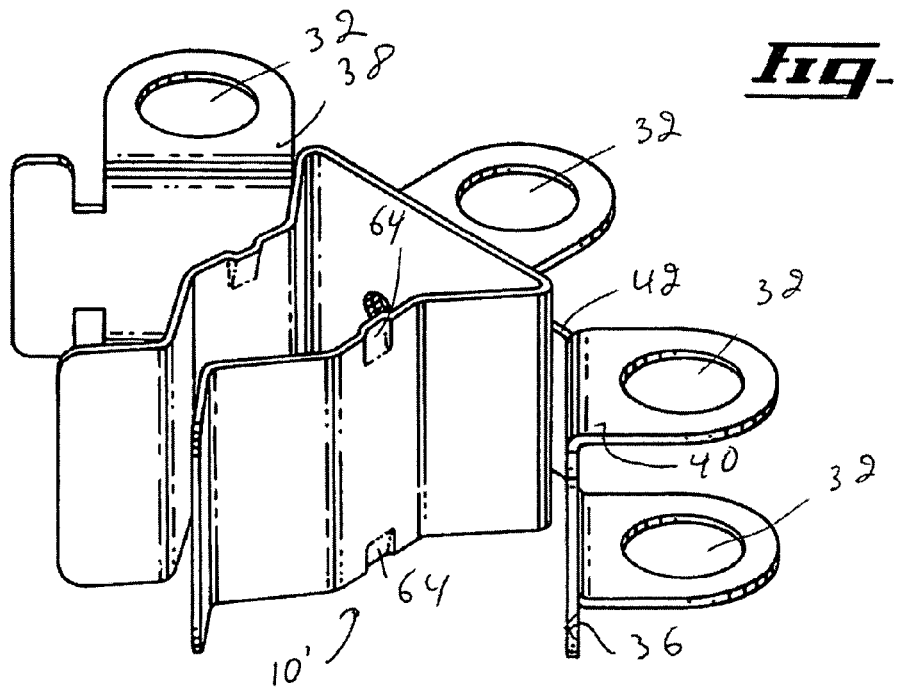
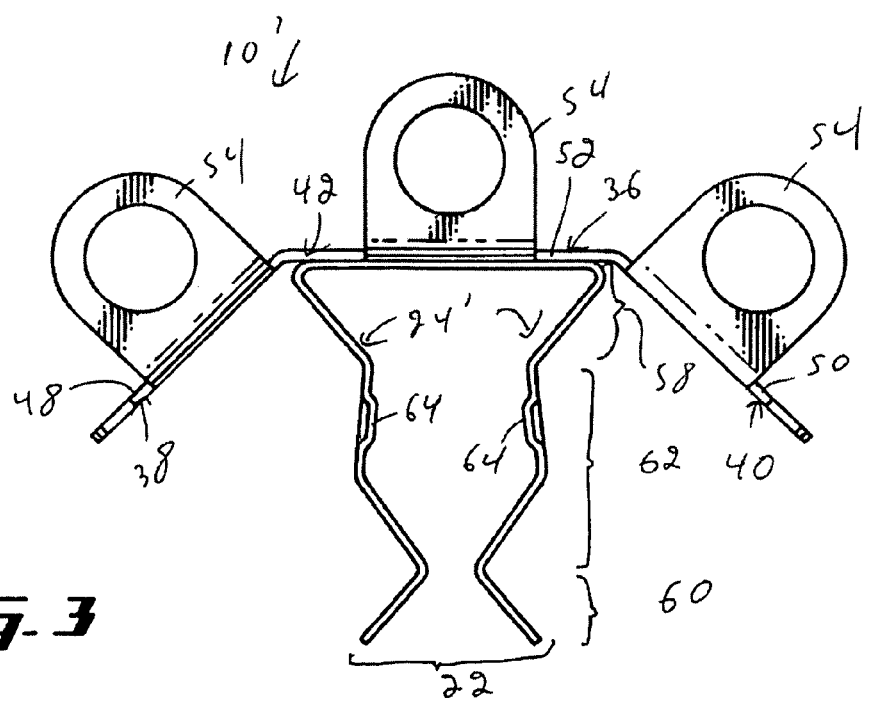

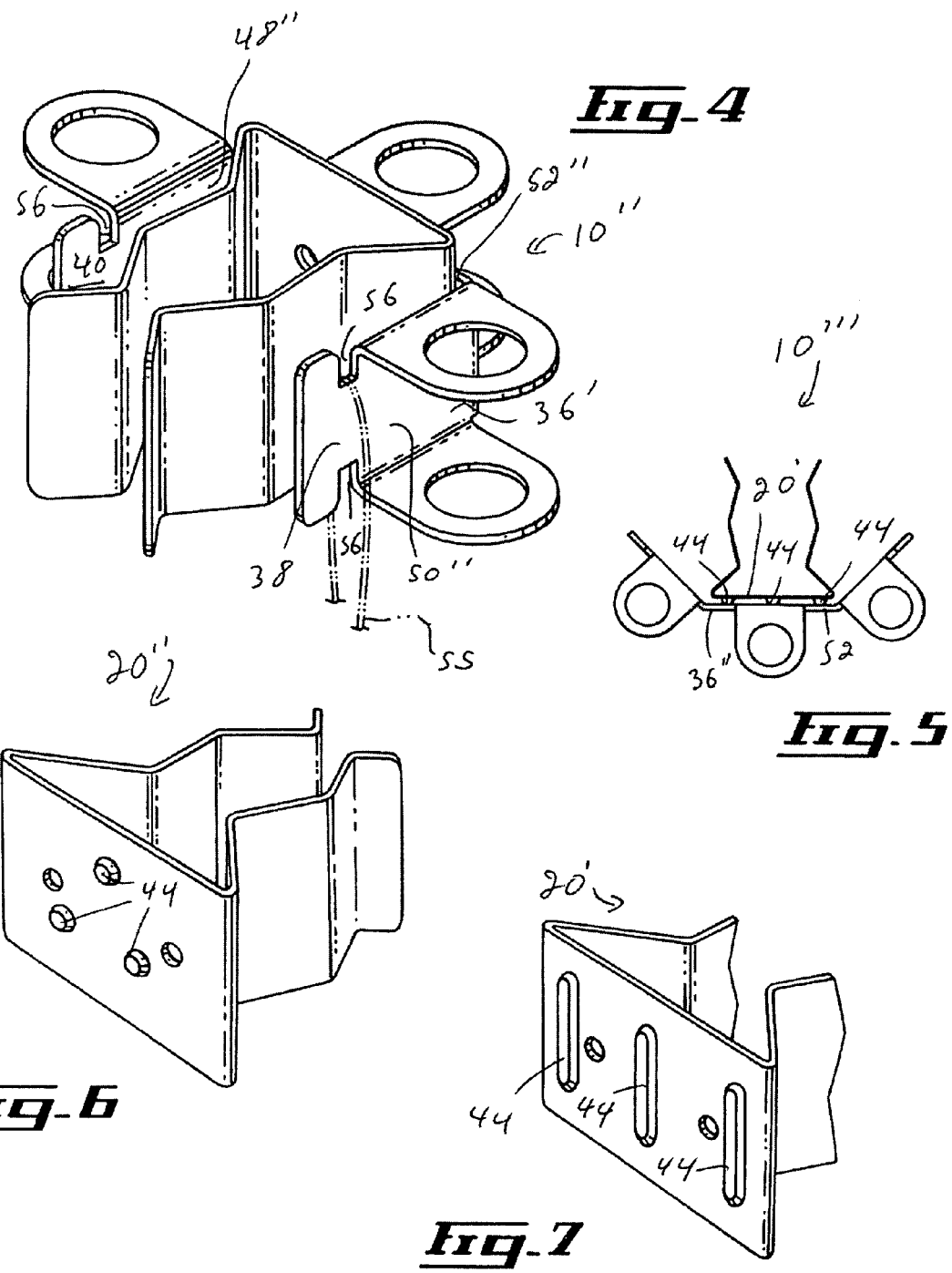

BAG SUPPORT

FIELD OF THE INVENTION

The present invention relates generally to equipment for supporting objects and is particularly concerned with a bag support.

BACKGROUND OF THE INVENTION

Medical bags such as drainage or catheter bags or drip bags are used extensively in the medical field along with so-called catheters. A catheter is a thin and flexible tube inserted into a bodily passage or cavity in order to allow fluids to pass into or out of it. The catheter is generally connected to a catheter bag or drainage bag which collects the fluids passing out. Alternatively, the catheter is connected to a drip bag which stores the fluids passing into the body. Catheterization is used in a variety of settings including hospitals, medical centers, care homes and the like typically for patients that are consigned to a bed or wheelchair.

Conventional drainage or drip bags are typically fabricated from polymeric resins and are typically not sufficiently rigid to support themselves in an upright position, for example, during collection of body fluids. Moreover, such containers may not be laid flat during collection because of the potential of leakage back through the fluid inlet port, with potential hazard to the patient. Furthermore, some bags also provide an accurate volume reading of the fluid connected, but to do so it is necessary that the bag be supported substantially vertically.

Examples of fluids collected by conventional drainage bags include body fluids resulting from surgery as well as urinary discharges. Since it is preferable to place the drainage below the patient for gravity flow, conventional drainage bags are typically suspended on the patient's bed, more particularly on the rail of the bed frame.

During typical hospital care, the patient, the bag and the patient's bed are frequently manipulated for performing various tasks necessary to care for the patient. In order to accomplish these tasks, it is necessary that, during these manipulations, the bag be retained in the desired orientation with respect to the ground. As mentioned previously, the bag typically hangs in a vertical orientation to permit accurate measurement of its fluid content and, for example, avoid fluid backflow to the patients. Also, the bag must be supported with reduced risks of falling off its support even when filled with drainage fluid. Some patients require multiple drainage bags and, hence, the challenges associated with appropriately supporting the drainage bags are multiplied.

Most conventional medical bags such as drainage bags include either an attachment ring or an attachment hook extending therefrom in order to allow the bag to be secured, typically to the railing of the bed frame.

So-called IV (intravenous) poles are also used extensively in a variety of medical settings. Such poles are typically used for securing drip bags at a level located above the patient in order to use gravity to bias the fluid out of the bag and into the patient's body. There exist a variety of situations wherein it is desirable to allow for both the drip and drainage bags to be secured to a common IV pole. For example, this would allow a patient to become ambulatory without requiring that the patient or care giving personnel carry the drainage bag. Also, mounting the drainage bag or bags on the IV pole would free up the bed frame and potentially lead to a reduced risk of entangling the catheters with a potential health hazard to the patient.

Accordingly, there exists a need for an improved bag support.

It is a general object of the present invention to provide such an improved bag support.

SUMMARY OF THE INVENTION

In a first broad aspect, the invention provides a bag support for supporting a bag, the bag support being mountable to a post, the bag having a pouch and a hook extending from the pouch. The bag support includes:
  a support body;
  a mounting clip for mounting the bag support to the post, the mounting clip including a pair of clip jaws extending substantially outwardly from the support body in a spaced apart relationship relatively to each other, the clip jaws defining a clip plane extending therebetween, the clip plane being substantially parallel to both of the clip jaws, the clip plane defining a longitudinal direction extending substantially perpendicularly to the clip plane;
  a hook receiving element extending from the support body, the hook receiving element defining a hook receiving aperture, the hook receiving aperture being substantially parallel to the clip plane;
  whereby inserting said post substantially longitudinally between said clip jaws allows the insertion of the hook into said hook receiving aperture so that the hook is substantially parallel to the post.

Advantages of the present invention include that the proposed bag support is designed so as to be readily mountable to supporting structures such as conventional IV poles. Also, the proposed bag support is designed so as to be mountable to conventional IV poles or the like through a set of quick and ergonomic steps without requiring special tooling or manual dexterity and without altering or damaging the IV pole or other supporting structure. Therefore, the proposed bag support is well suited for use with medical bags, among other possibilities.

Also, the proposed bag support may be easily retrofitted to IV poles or the like having a variety of shapes and sizes.

Still furthermore, the proposed bag support is designed so as to be usable for supporting a variety of medical bags including drip, catheter or drainage bags of various shapes and sizes. Also, the proposed bag support allows for medical bags having both attachment hooks and attachment rings extending therefrom to be readily installed on the bag support again through a set of quick and ergonomic steps and without requiring manual dexterity. The proposed bag support allows for quick engagement and disengagement of the medical bag onto and away from the bag support with reduced risks of damaging the medical bag.

Furthermore, the proposed bag support is designed so as to allow more than one medical bag to be attached thereto with reduced risks of interference between the bags and their corresponding catheters. Still furthermore, the proposed bag support is designed so as to be relatively compact so as to reduce the risks of interference both during shipping and storage and in actual use.

Yet, still furthermore, the proposed bag support is designed so as to be manufacturable using conventional forms of manufacturing so as to provide a bag support that will be economically feasible, long-lasting and relatively trouble-free in operation.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

An embodiment of the present invention will now be disclosed, by way of example, in reference to the following drawings in which:

FIG. 2, in a perspective view, illustrates a bag support in accordance with an alternative embodiment of the present invention.

FIG. 3, in a top plan view, illustrates the bag support of FIG. 2;

FIG. 4, in a perspective view, illustrates a bag support in accordance with another alternative embodiment of the present invention;

FIG. 5, in a top plan view, illustrates a bag support in accordance with an yet another alternative embodiment of the present invention;

FIG. 6, in a perspective view, illustrates a base and a clip of a bag support in accordance with yet another alternative embodiment of the present invention; and FIG. 7, in a perspective view, illustrates a support body of the bag support of FIG. 5.

DETAILED DESCRIPTION

Figure 1:
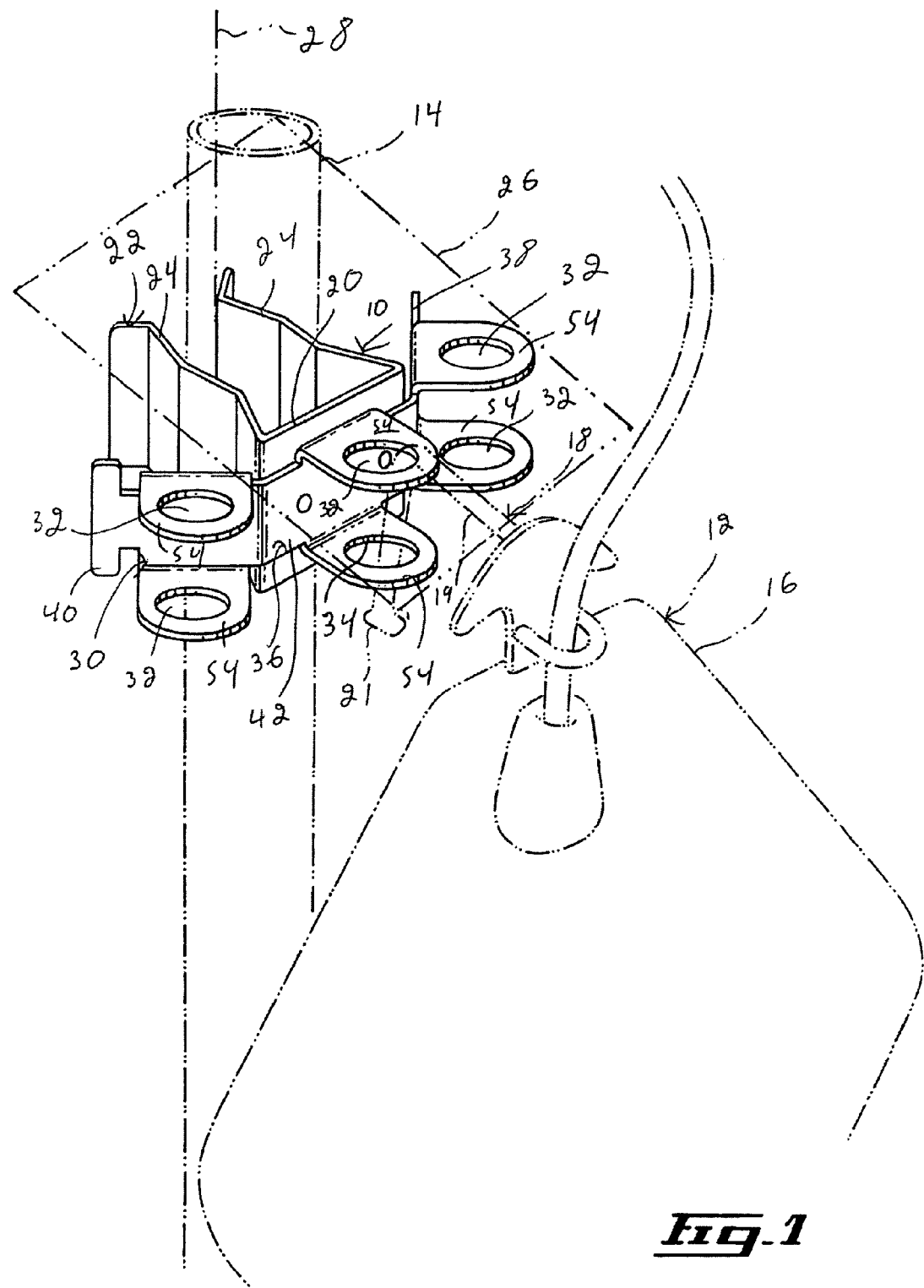
FIG. 1, in a perspective view, illustrates a bag support in accordance with an embodiment of the present invention.

FIG. 1 illustrates a bag support 10 for supporting a bag 12. The bag support 10 is shown mounted a post 14. However, the reader skilled in the art will readily appreciate that the bag support 10 is mountable to any other suitable supporting structure.

The bag 12 includes a pouch 16 and a hook 18 extending from the pouch 16. In some embodiments of the invention, as shown in FIG. 1, the hook 18 is substantially L-shaped and includes a hook proximal segment 19 extending from the pouch 16 and a hook distal segment 21 extending substantially perpendicularly from the hook proximal segment substantially opposed to the pouch 16. The hook distal segment 21 extends through a hook receiving aperture formed into the bag support 10, as described in further details hereinbelow.

In some embodiments of the invention, the bag 12 is a medical bag for receiving a body fluid. In other embodiments of the invention, the bag 12 is a medical bag for delivering a medical fluid to be injected intravenously into an intended user. In yet other embodiments of the invention, the bag 12 is any other suitable bag.

The bag support 10 includes a mounting clip 22 for mounting the bag support 10 to the post 14. The mounting clip 22 includes a pair of clip jaws 24 extending substantially outwardly from a support body 20 in a spaced apart relationship restively to each other. The clip jaws 24 define a clip plane 26 extending therebetween. The clip plane 26 is substantially parallel to both of the clip jaws 24. The clip plane also defines a longitudinal direction 28 extending substantially perpendicularly to the clip plane 26.

The bag support 10 includes a hook receiving element 30 extending from the support body 20. The hook receiving element 30 defines a hook receiving aperture 32. The hook receiving aperture 32 is substantially parallel to the clip plane 26.

Inserting the post 14 substantially longitudinally between the clip jaws 22 allows the insertion of the hook 18 into the hook receiving aperture 32 so that the hook 18 is substantially parallel to the post 14. In some embodiments of the invention, the hook distal segment is supported substantially parallel to the post 14 when the hook 18 is supported into the bag support 10.

In some embodiments of the invention, as shown in FIG. 1, the hook receiving element 30 defines a hook abutment surface 34, the hook abutment surface 34 being provided for abutting against the hook 18 when the hook 18 is inserted through the hook receiving aperture 32. In embodiments of the invention wherein the hook 18 includes the hook distal segment 21, the hook distal segment 21 abuts against the hook abutment surface 34 when the hook 18 is supported by the bag support 10.

In the embodiment of the invention shown in the drawings, the hook abutment surface 34 is defined at the periphery of another hook receiving aperture 32 defines by the hook receiving element 30. In these embodiments, the hook receiving element 30 defines a pair of hook receiving apertures 32, the hook receiving apertures 32 being each substantially parallel to the clip plan 26. The hook receiving apertures 32 are substantially in register with each other and substantially longitudinally spaced-apart from each other.

The hook receiving element 30 includes a receiving element base 36. In some embodiments of the invention, for example in the bag support 10 illustrated in FIG. 1, the bag support 10' illustrated in FIGS. 2 and 3 and the bag support 10''' illustrated in FIG. 4, the receiving element base 36 and 36' extends from the support body 20. In other embodiments of the invention, for example in the bag support 10''' illustrated in FIG. 5, the receiving element base 36' is substantially spaced-apart from the support body 20.

As better shown in FIG. 3, the receiving element base 36 includes a base first lateral segment 38, a base second lateral segment 40 substantially opposed to the base first lateral segment 38 and a base central segment 42 extending therebetween. For example, the base first lateral, second lateral and central segments 38, 40 and 42 are each substantially plate-shaped. In these embodiments, the base first lateral segment 38 includes a first lateral plate 48, the base second lateral segment 40 includes a second lateral plate 50 and the base central segment 42 includes a central plate 52.

In some embodiments of the invention, the base first and second lateral segments 38 and 40 are angled towards the clip 22 relatively to the base central segment 42. In embodiments of the invention wherein the base first lateral, second lateral and central segments 38, 40 and 42 include respectively the first lateral, the second lateral and the central plates 48, 50 and 52, the first lateral and second lateral plates extend from the central plate 52 and are angled at an angle of between about 30 degrees and about 60 degrees, and in a specific example at about 45 degrees relatively to the central plate 52.

However, in alternative embodiments of the invention, the base first lateral and second lateral segments 38 and 40 are angled at any other angle relatively to the base central segment 42 and may also take any other suitable shape. For example, FIG. 4 illustrates an alternative bag support 10'' wherein lateral plates 48'' and 50'' are angled at about 90 degrees relatively to a central plate 52''.

In some embodiments of the invention, for example in the embodiment of the invention shown in FIG. 1, each of the base central, first lateral and second lateral segments 38, 40 and 42 each define a respective pair of hook receiving apertures 32 that are substantially in register with each other, extend in a plane substantially parallel to the clip plane 26 and are in a substantially longitudinally spaced-apart from each other. For example, each of the hook receiving apertures 32 is formed into a respective flange 54 extending substantially parallel to the clip plane 26 and substantially away from the clip jaws 24. As seen in FIG. 3, the flanges 54 extend from the first lateral, second lateral and central plates 48, 50 and 52.

While a bag support can include six flanges 54 as shown in the drawing, it is within the scope of the invention to have bag supports similar to the bag support 10 that include any suitable number of flanges.

In some embodiments of the invention, for example for the bag support 10" shown in FIG. 4, the bag support 10" may be used with bags that are suspendable using a loop of material such as, for example, a rope 55. In these embodiments, notches 56 may extend substantially longitudinally into the base first and second lateral segments 38 and 40. For example, the notches 56 are each provided pair-wise substantially in register with each other and substantially longitudinally spaced-apart from each other. The notches 56 extend towards each other into the base first and second lateral segments 38 and 40.

In some embodiments of the invention, as shown in FIGS. 5, 6 and 7, the base central plate 52 is substantially spaced-apart from the support body 20', 20". To that effect, base protrusions 44 extend between the base central segment 42 and the support body 20', 20".

As shown in FIGS. 5 and 7, the base protrusions 44 may be substantially elongated and may extend substantially longitudinally between the support body 20' and the base central segment 42. For example, the base protrusions 44 extend integrally from the support body 20'.

As shown in FIG. 6, in alternative embodiments of the invention, the base protrusions 44' are substantially conical and are provided in any suitable number and any suitable geometrical arrangement. For example, three base protrusions 44' are located at the vertices of a substantially equilateral triangle and extend integrally from the support body 20". Also, in other embodiments of the invention, the base protrusions may take any other suitable shape.

In some embodiments of the invention, the support body 20, 20', 20" is substantially plate-shaped and is secured to the base central segment 42 using rivets. However, the support body 20 and the base central segment 42 may be secured to each other in any suitable manner, for example by being welded to each other.

An example of the clip jaws 24' usable with the present invention is better illustrated in FIG. 3. These clip jaws include each a respective jaw proximal segment 58 located substantially adjacent the support body 20 and a respective jaw distal segment 60 located distally relatively to the support body 20. Each of the clip jaws 24 also includes a respective jaw central segment 62 extending between the jaw proximal and distal segments 58 and 60.

In some embodiments of the invention, the jaw distal segments 60 taper toward each other in a direction leading towards the support body 20. Also, the jaw central segments 62 are substantially concave in a plane substantially parallel to the clip plan 26 and are oriented so as to taper in a direction leading away from each other. In a specific embodiment of the invention, the jaw central segments 62 are substantially V-shaped. However, the jaw central segments may have any other suitable shape without departing from the scope of the invention.

In a variant shown in FIGS. 2 and 3, each of the jaw central segment 62 includes jaw protrusions 64 extending substantially outwardly therefrom toward the other one of the jaw central segments 62. For example, the jaw protrusions 64 are provided pair-wise substantially longitudinally opposed relatively to each other and are formed integrally into the jaw central segment 62, as better illustrated in FIG. 2.

In use, the bag support 10 is mounted to the post 14 as follows. First, the jaw distal segments 60 are abutted against the post 14. Exerting a force onto the bag support 10 directed towards the post 14 forces the two clip jaws 24 apart from each other. After the exertion of a predetermined force onto the bag support 10, the post 14 is received between the jaw central segments 62. This causes the clip jaws 24 to exert a force onto the post 14 so that the bag support 10 remains at a fixed location relatively to the post 14 even under the influence of longitudinal forces.

In embodiments of the invention wherein the jaw protrusions 64 are present, the jaw protrusions 64 may bite into the material composing the post 14, therefore increasing the resistance to longitudinal movements of the bag support 10 relatively to the post 14.

Indeed, it is often desirable in a hospital environment that the material used to manufacture equipment be stainless steel as it has good biological compatibility and high resistance to disinfecting and other sanitizing treatments. In these cases, having a bag support made of stainless steel clipping onto a post 14 made of stainless steel may cause relatively small frictional forces between the bag support 10 and the post 14, which may lead to the bag support 10 sliding relatively to the post 14 under the weight of medical bags 12 secured to the bag support 10. The jaw protrusions 64 help in preventing these relative movements between the bag support 10 and the post 14.

In embodiments of the invention wherein only one bag 12 is attached to the support 10, the jaw protrusions 64 may not be necessary as the weight of the bag 12 and bag support 10 assembly is then relatively small.

After the bag support 10 has been mounted to the post 14, the bag 12 may be attached to the bag support 10. To that effect, in embodiments of the invention wherein the hook 18 is substantially L-shaped, the hook distal segment 21 is inserted into two substantially longitudinally spaced-apart hook receiving apertures 32. If the post 14 is substantially vertical, the hook 18 is supported by one of the hook receiving apertures that is located upwardly relatively to the other hook receiving aperture 32. Then, the weight of the bag 12 inclines the hook distal segment 21 until the hook distal segment 21 abuts against the hook abutment surface 34 formed by the lower hook receiving aperture 32.

Therefore, the hook 18 is relatively easily mounted to the bag support 10, relatively easily removed from the bag support 10 while being relatively stably support into the bag support 10. Furthermore, in embodiments of the invention wherein the hook 18 is substantially L-shaped and substantially rigidly attached to the pouch 16, the bag support 10 allows to support the bag 12 in a substantially vertical orientation, which prevents spills from the medical bag 12 and allows medical personnel to detect the degree to which the bag 12 is spilled relatively easily.

The angulation between the base first lateral and second lateral segments 38 and 40 and the base central segment 42 allows to support more than one bag 12 onto the same bag support 10 in a relatively compact manner. In addition, this angulation allows supporting the bag 12 relatively close to the post 14, which reduces any torque that may be exerted by the bag 12 onto the post 14, therefore improving the stability of the combination bag support 10 and bag 12.

As shown in FIG. 4, if desired, a rope 55 may be inserted through the notches 56 to attach other types of medical bags to the bag support 10. In addition, although not shown in the drawings, the bag support 10 is suitable for receiving bags having hooks 18 that have alternative shapes without departing from the scope of the invention.

In embodiments of the invention wherein the support body 20 is substantially spaced apart from the receiving element base 36, the bag support 10 is relatively easily cleaned from fluid that may spill onto the support body or the receiving element base using, for example, pressurized water.

Although the present invention has been described hereinabove by way of preferred embodiments thereof, it can be modified, without departing from the spirit and nature of the subject invention as defined in the appended claims.

What is claimed is:

1. A bag support for supporting a bag, said bag support being mountable to a post, the bag having a pouch and a hook extending from the pouch, said bag support comprising:
   a support body;
   a mounting clip for mounting said bag support to the post, said mounting clip including a pair of clip jaws extending substantially outwardly from said support body in a spaced apart relationship relatively to each other, said clip jaws defining a clip plane extending therebetween, said clip plane being substantially parallel to both of said clip jaws, said clip plane defining a longitudinal direction extending substantially perpendicularly to said clip plane;
   a hook receiving element extending from said support body, said hook receiving element defining a hook receiving aperture, said hook receiving aperture being substantially parallel to said clip plane;
   whereby inserting said post substantially longitudinally between said clip jaws allows the insertion of the hook into said hook receiving aperture so that the hook is substantially parallel to the post; said hook receiving element defining a hook abutment surface substantially longitudinally spaced apart from said hook receiving aperture, said hook abutment surface being provided for abutting against said hook when said hook is inserted through said hook receiving aperture; said hook receiving element also defining a pair of hook receiving apertures, said hook receiving apertures being each substantially parallel to said clip plane, said hook receiving apertures being substantially in register with each other and substantially longitudinally spaced apart from each other; wherein said receiving element base includes a base first lateral segment, a base second lateral segment substantially opposed to said base first lateral segment and a base central segment extending therebetween, said base first and second lateral segments being angled towards said clip relatively to said base central segment.

2. A bag support as defined in claim 1, wherein said base first and second lateral segments are angled at an angle of between about 30 degrees and about 60 degrees relatively to said base central segment.

3. A bag support as defined in claim 1, wherein said base central segment is substantially spaced apart from said support body, said receiving element base including base protrusions extending between said base central segment and said support body.

4. A bag support as defined in claim 3, wherein each of said base central, first lateral and second lateral segments defines a respective hook receiving aperture, said hook receiving apertures being substantially parallel to said clip plane.

5. A bag support as defined in claim 4, wherein said hook receiving apertures are each formed in a respective flange extending substantially parallel to said clip plane and substantially away from said clip jaws.

6. A bag support as defined in claim 1, wherein at least one of said base first and second lateral segments defines a notch extending substantially longitudinally thereinto.

7. A bag support as defined in claim 1, wherein at least one of said base first and second lateral segments defines a pair of substantially longitudinally opposed notches extending substantially longitudinally thereinto.

8. A bag support for supporting a bag, said bag support being mountable to a post, the bag having a pouch and a hook extending from the pouch, said baa support comprising:
   a support body;
   a mounting clip for mounting said bag support to the post, said mounting clip including a pair of clip jaws extending substantially outwardly from said support body in a spaced apart relationship relatively to each other, said clip jaws defining a clip plane extending therebetween, said clip plane being substantially parallel to both of said clip jaws, said clip plane defining a longitudinal direction extending substantially perpendicularly to said clip plane;
   a hook receiving element extending from said support body, said hook receiving element defining a hook receiving aperture, said hook receiving aperture being substantially parallel to said clip plane;
   whereby inserting said post substantially longitudinally between said clip jaws allows the insertion of the hook into said hook receiving aperture so that the hook is substantially parallel to the post; said hook receiving element defining a hook abutment surface substantially longitudinally spaced apart from said hook receiving aperture, said hook abutment surface being provided for abutting against said hook when said hook is inserted through said hook receiving aperture; said hook receiving element also defining a pair of hook receiving apertures, said hook receiving apertures being each substantially parallel to said clip plane, said hook receiving apertures being substantially in register with each other and substantially longitudinally spaced apart from each other; wherein said clip jaws each define a respective jaw distal segment located distally relatively to said support body, said jaw distal segments tapering towards each other in a direction leading towards said support body and said clip jaws each define a respective jaw proximal segment located substantially adjacent said support body and a respective jaw central segment extending between said jaw proximal and distal segments, said jaw central segments being substantially concave in a plane substantially parallel to said clip plane, each of said jaw central segment being oriented so as to taper in a direction leading away from the other one of said jaw central segment.

9. A bag support as defined in claim 8, wherein said jaw central segments are each substantially V-shaped.

10. A bag support as defined in claim 8, wherein at least one of said jaw central segments includes a jaw protrusion extending substantially outwardly towards the other one of said jaw central segments.

11. A bag support as defined in claim 10, wherein at least one of said jaw central segments includes a pair of substantially longitudinally spaced apart jaw protrusions extending substantially outwardly towards the other one of said jaw central segments.

* * * * *